United States Patent
Wall

Patent Number: 5,824,038
Date of Patent: Oct. 20, 1998

[54] ANGIOPLASTY STENT

[76] Inventor: W. Henry Wall, 1004 P Oak Chase Dr., Tucker, Ga. 30084

[21] Appl. No.: 578,504

[22] Filed: Dec. 26, 1995

Related U.S. Application Data

[63] Continuation of Ser. No. 129,834, Dec. 8, 1987.

[51] Int. Cl.⁶ ..................................................... A61F 2/06
[52] U.S. Cl. ................................................................. 623/1
[58] Field of Search ............................................. 623/1, 11

[56] References Cited

U.S. PATENT DOCUMENTS

| | | |
|---|---|---|
| 4,140,126 | 2/1979 | Choudhury . |
| 4,577,637 | 3/1986 | Mueller, Jr. . |
| 4,617,932 | 10/1986 | Kornberg . |
| 4,647,416 | 3/1987 | Seiler, Jr. et al. ............ 623/1 |
| 4,740,207 | 4/1988 | Kreamer . |
| 4,800,882 | 1/1989 | Gianturco . |
| 4,820,298 | 4/1989 | Leveen et al. ................ 623/1 |
| 4,944,740 | 7/1990 | Buchibinder et al. . |
| 4,969,890 | 11/1990 | Sugita et al. . |
| 5,007,926 | 4/1991 | Derbyshire ................... 623/1 |
| 5,059,211 | 10/1991 | Stack et al. ................... 623/1 |
| 5,102,417 | 4/1992 | Palmaz . |

*Primary Examiner*—David Isabella
*Attorney, Agent, or Firm*—Wilson Sonsini Goodrich & Rosati

[57] ABSTRACT

A prosthesis for use in preventing re-stenosis after angioplasty is formed of plastic or sheet metal, and is expandable and contractible for placement. The prosthesis can be inserted while in a collapsed position, then expanded and locked at the larger diameter. Spring force can be provided by the material itself, or metal springs can be embedded within the walls of the prosthesis. Preferably, the walls have holes therethrough to promote tissue growth; and, in one embodiment, the holes are in the form of slots so that the prosthesis is segmented and can bend longitudinally.

5 Claims, 2 Drawing Sheets

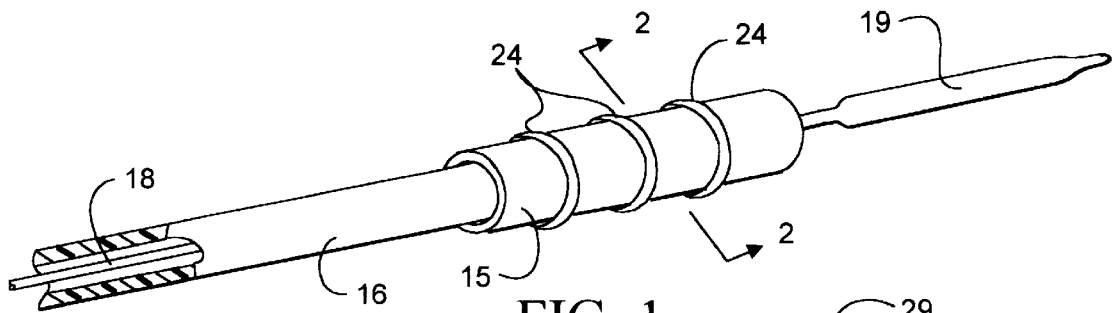
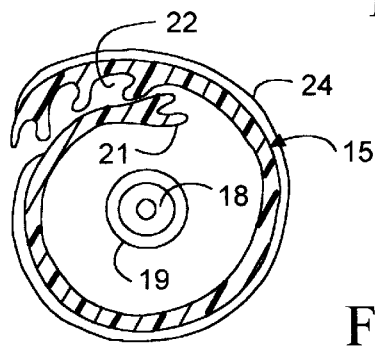
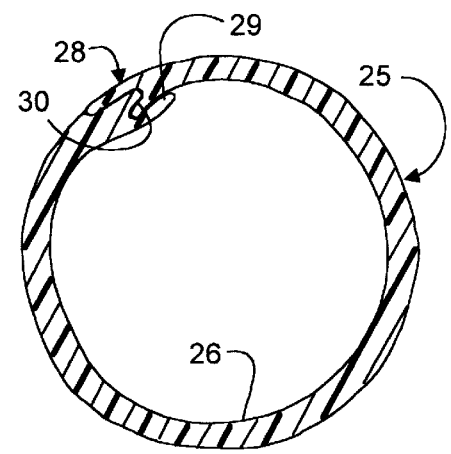
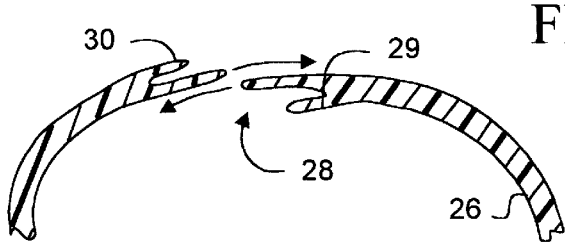
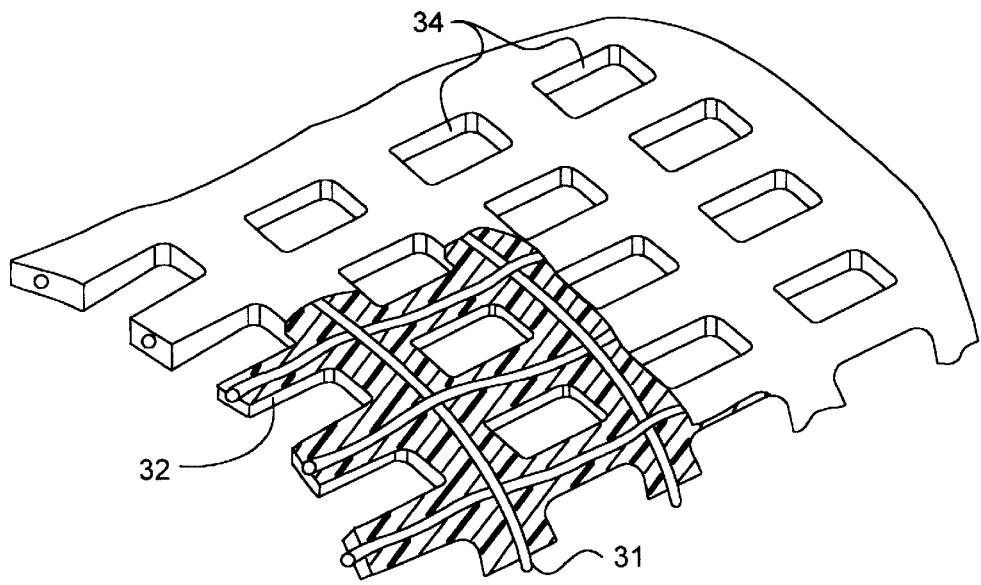

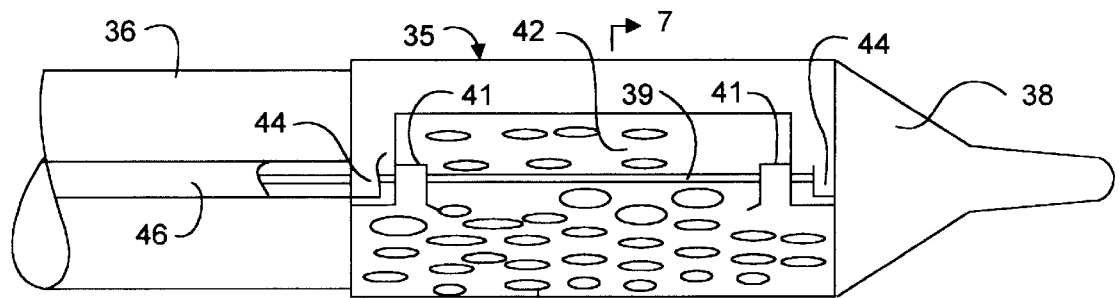
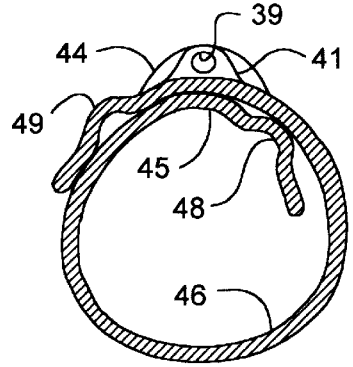
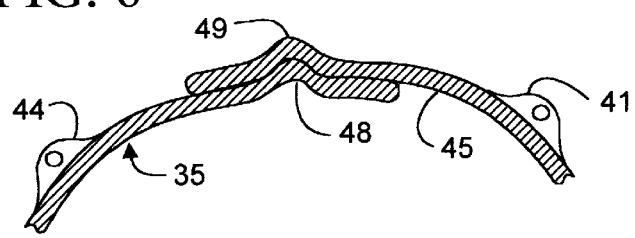
FIG. 6
FIG. 7
FIG. 8
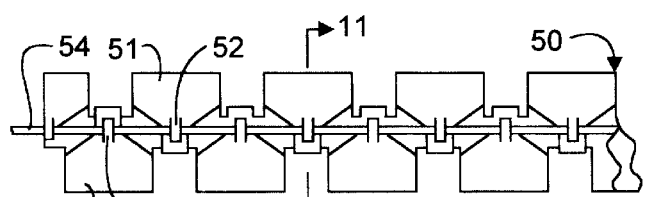
FIG. 9
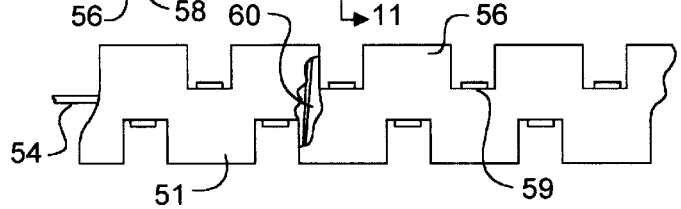
FIG. 10
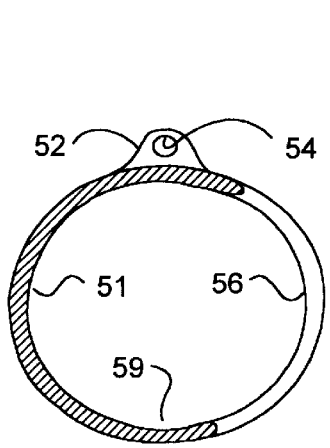
FIG. 11
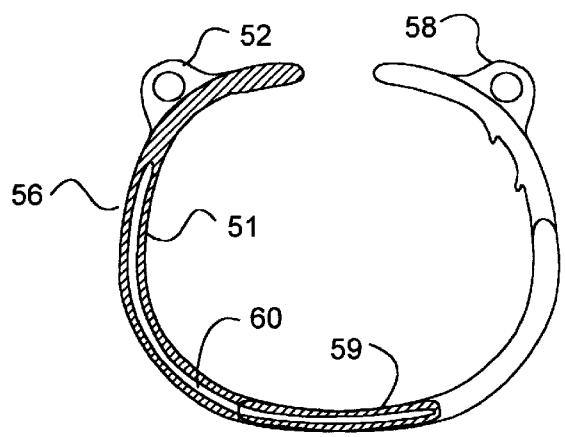
FIG. 12

ANGIOPLASTY STENT

CROSS REFERENCE

This application is a continuation of U.S. application Ser. No. 07/129,834 filed Dec. 8, 1987.

INFORMATION DISCLOSURE STATEMENT

There has been considerable use of balloon angioplasty due to stenosis in arteries having atherosclerotic plaque and the like in an effort to enlarge the lumen and to provide adequate blood flow. While such angioplasty has been successful, it has been found that in many cases re-stenosis requires that the procedure be repeated.

More recently, there have been efforts at following the balloon angioplasty with placement of a stent, the stent being in the nature of a sleeve that will mechanically maintain some minimum lumen diameter.

It will be obvious that, in order to place a stent utilizing the balloon angioplasty technology, the stent must necessarily have a sufficiently small external diameter to be moved into the desired area by some means such as a catheter, then to be expanded, both to be held in place by the arterial elasticity and to provide the minimum lumen diameter. Prior stents have generally taken the form of wire mesh that is collapsed for placement into the artery, then expanded, either by means of a balloon or by its own elasticity. The stent is generally held in place simply by the arterial elasticity in the first instance, and it has been found that epithelialization takes place throughout the stent so that the entire stent becomes effectively embedded in the vessel wall.

The prior art stents, being woven stainless steel wire or the like tend not to be very flexible longitudinally so that their primary use is in straight portions of vessels. Also, inflation of the balloon is required to expand the wire to its desired size in some cases, while other wire mesh stents tend to take a particular size, and must be held by a sleeve or the like during placement.

SUMMARY OF THE INVENTION

This invention relates generally to prostheses, and is more particularly concerned with a prosthesis in the form of a stent to be placed in a vessel for mechanically maintaining an opening.

This invention provides a stent for maintaining a minimum opening through an artery or the like, the stent being in the form of a sleeve having a discontinuity so the sleeve has a collapsed position to be assumed during placement of the stent, and an expanded position for use in its final location for maintaining the desired opening. In one embodiment of the invention, the stent may be carried by one catheter while a second coaxial catheter in the nature of a conventional balloon catheter is carried therein. This arrangement allows use of the balloon catheter to provide a mechanical opening in the vessel, then to allow the stent to be slipped into place over the balloon. The balloon can then be used to manipulate the stent for any necessary opening of the stent and disengagement of the stent from the coaxial catheter. It is also contemplated that the stent of the present invention can be carried by a single, generally conventional balloon catheter.

The stent of the present invention may selectively be biased towards a closed position and lockable in an open position, or biased in an open position and lockable in a closed position. In the former case, the stent will be put into place in its collapsed condition, then forcibly expanded by a balloon or the like to the desired locked condition. In the latter case, the stent may be held by a pin or the like in its collapsed condition, and the pin removed to allow the stent to assume its open position.

The stent of the present invention may be made from any numerous materials, including metal or the like, and also including various plastic materials. The plastic materials may be simply homogeneous molded plastics, or may comprise a plastic covering over a knit or woven mesh. The knit or woven mesh may, in turn, be metal or plastic. The precise material can be selected to achieve the desired features of the stent.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing one form of stent made in accordance with the present invention and carried by a coaxial catheter;

FIG. 2 is an enlarged cross-sectional view taken substantially along the line 2—2 in FIG. 1;

FIG. 3 is a cross-sectional view of a slightly modified form of stent shown in its open and locked position;

FIG. 4 is a fragmentary view showing the stent of FIG. 3 after expansion beyond its maximum, open position;

FIG. 5 is a fragmentary perspective view, partially in cross-section, showing one form of material for use in constructing the stents of the present invention;

FIG. 6 is an elevational view showing another modified form of stent made in accordance with the present invention, the stent being carried on a catheter;

FIG. 7 is a cross-sectional view taken substantially along the line 7—7 in FIG. 6;

FIG. 8 is a fragmentary view showing the stent of FIG. 7 after expansion;

FIG. 9 is a top plan view of another modified form of stent made in accordance with the present invention, the stent being shown without the carrying catheter;

FIG. 10 is a bottom plan view of the device shown in FIG. 9;

FIG. 11 is an enlarged cross-sectional view taken substantially along the line 11—11 in FIG. 9; and, FIG. 12 is a view similar to FIG. 11 but showing the stent in its expanded condition.

DETAILED DESCRIPTION OF THE EMBODIMENTS

Referring now more particularly to the drawings, and those embodiments of the invention here presented by way of illustration, FIG. 1 shows a stent generally indicated at 15, the stent 15 being carried by a catheter 16. The catheter 16 is one of two coaxial catheters, the other catheter 18 being a generally conventional balloon catheter having the balloon 19 at its distal end.

It will be understood by those skilled in the art that, in conventional, balloon angioplasty, a catheter such as the catheter 18 is threaded through the arterial system to place the balloon at the location of the stenosis. The balloon 19 is then inflated to urge the arterial wall outwardly and open the lumen in the artery. This same technique will be utilized with the arrangement shown in FIG. 1 of the drawings, the balloon 19 acting to perform the angioplasty; however, after the vessel is sufficiently open by means of the balloon 19, the coaxial catheter 16 will be manipulated to urge the stent 15 in place over the balloon 19. After the stent 15 is over the balloon 19, the balloon 19 will be inflated to urge the stent outwardly to its opened condition.

Referring to FIG. 2 of the drawings, it will be seen that the stent 15 includes a wall 20, the wall 20 having sufficient memory that the stent as a whole tends to maintain its collapsed condition. One end of the wall 20 is provided with a hook 21 for engagement with one of a plurality of complementary hook means 22. The hook 21 will necessarily be biased outwardly sufficiently that, as the hook 21 is urged past the plurality of hook means 22, the hook 21 will engage each of the hooks 22. Because of this arrangement, when the balloon 19 is not further inflated, the hook 21 will remain engaged with one of the hooks 22 to prevent collapse of the stent 15.

It will also be noticed that the stent 15 contains a plurality of generally circumferential ribs 24. It is contemplated that the ribs 24 will engage the arterial walls sufficiently to prevent inadvertent movement of the stent after placement and removal of the catheter 16. As will be discussed hereinafter, the stent 15 may also contain a plurality of openings to allow tissue to grow therethrough and further hold the stent 15 in place.

Looking now at FIGS. 3 and 4 of the drawings, it will be seen that the stent 25 is a slightly modified form of the stent 15. The stent 25 includes the wall 26 which will be biased towards collapse as is the wall 20 of the stent 15. Once the stent 25 is urged to its expanded condition, the interlocking hook means 28 will become engaged as shown in FIG. 3 to prevent collapse of the stent 25 and maintain the stent in its maximum, open condition.

It will be understood that there may be times when the stent is improperly placed, or for other reasons must be removed. With the stent 25, the ends 29 and 30 of the wall 26 are so biased that, when the stent 25 is expanded so far that the ends 29 and 30 are released from engagement, the end 29 will move inwardly and the end 30 will move outwardly. On subsequent release of the stent 25, the walls 29 and 30 have exchanged places so that the hook means 28 cannot now engage. As a result, the stent 25 will collapse to its minimum external diameter.

Though many different materials may be utilized in forming the stents of the present invention, one form of material is illustrated in FIG. 5 of the drawings. In FIG. 5 there is a woven network indicated at 31. This woven network may be metal such as stainless steel or the like, or may be a knit or woven plastic material such as polyester filaments. If the network 31 is made of metal, the intersections can be sonically welded or otherwise heat sealed to one another.

Following provision of the network 31, the network 31 is covered by a plastic material indicated at 32. The material 32 can again be any of numerous materials, so long as the material is implantable. Nevertheless, numerous plastic materials including polyethylene, polyester, polytetraflouroethylene and others can be utilized.

As illustrated in FIG. 5, the network 32 is simply coated with the material 32 so that openings 34 are distributed throughout the material. While the openings 34 are not necessarily so uniformly distributed, it will be understood that the use of a plurality of openings 34 promotes epithelialization to promote incorporation of the stent into the vessel wall.

Turning now to FIG. 6 of the drawings, there is a stent indicated at 35 carried at the end of a catheter 36. The catheter 36 includes a balloon 38 as is known in the art.

While the above described stents have been biased inwardly and have been forced outwardly, the stent 35 is biased outwardly and is forced inwardly and retained by means of a pin 39. For a full understanding of the stent 35, attention is directed to FIGS. 6, 7 and 8 of the drawings which show both plan view and cross-sectional views of the stent 35.

The stent 35 is here shown as having a generally smooth wall 40 having a plurality of openings 43 in accordance with the foregoing discussion. The wall 40 is biased outwardly towards it maximum diameter; however, for placement by means of the catheter 36, the stent 35 is urged inwardly to its minimum diameter, and the stent is provided with a first pair of lugs 41 carried on the end 42 of the wall 40, and second pair of lugs 44 carried generally towards the opposite end 45 of the wall 40. When the wall 40 is urged inwardly to collapse the stent 35, appropriate openings in the lugs 41 and 44 are aligned, and the pin 39 is placed therethrough to hold the stent 35 in its collapsed position.

As is shown in FIG. 6 of the drawings, it is contemplated that the pin 39 will be in the form of a wire that extends along the catheter 36, contained within a channel 46. With this arrangement, the pin 39 will extend to the lug 44 at the distal end of the stent 35, and it will be understood that the distal end lug 44 may have a hole that does not extend completely through the lug in order to cover the end of the pin 39. The pin 39 then extends the full length of the stent 35 and into the channel 46. While not here illustrated, it will be understood that the pin 39 extends completely along the length of the catheter 36 so the pin 39 can be manipulated externally of the body so that, at the appropriate moment, the pin 39 can be removed from the lugs 41 and 44 and allow the stent 35 to expand.

As here shown, when the stent 35 expands, the ends 42 and 45 will remain overlapped to some extent. If desired, interlocking grooves 48 and 49 can be provided so the stent 35 has a relatively fixed expanded diameter.

Attention is next directed to FIGS. 9–12 of the drawings which show another modified form of stent. The stent 50 is similar to the stent 35 in that it is biased outwardly and is forcibly held inward by a pin; however, the stent 50 is considerably different from the stent 35 in that the stent 50 is of a somewhat segmented construction to allow longitudinal flexibility.

In the top plan view shown in FIG. 9 of the drawings, it will be seen that the stent 50 includes a plurality of segments 51, each segment 51 having a lug 52 thereon for receipt of a pin 54. The segments 51 are interspersed with segments 56 on the opposite side of the pin 54, the segments 56 having lugs 58 thereon. As is better shown in FIG. 10 of the drawings, there is a generally continuous spine 59 extending along the bottom of the stent 50 and interconnecting all of the segments 51 and 56. Because of this construction, it will be seen that the stent 50 will be readily bendable along its longitudinal axis, the bending being resisted only by the relatively narrow spine 59. Furthermore, it will be understood that the individual segments 51 and 56 can be made much shorter to provide for tighter radii, or relatively long in the event the stent is not intended to be very flexible.

Though the stent 50 in FIGS. 9–12 of the drawings is not shown in conjunction with a catheter, it will be understood by those skilled in the art that the stent will be put into place using an arrangement such as that shown in FIG. 6 of the drawings. The catheter 36 and wire channel 46 would be the same, the specific stent being the only difference.

FIG. 11 of the drawings shows the cross-sectional shape of the stent 50 while the stent is held in its closed, or collapsed, condition by the pin 54. When the pin 54 is removed, the stent 50 will expand to the condition shown in FIG. 12 of the drawings. It will of course be recognized that a balloon, such as the balloon 38, may be utilized to assist in urging the walls of the stent outwardly to the desired position.

The material from which the stent 50 is made may be any of the numerous materials previously mentioned, including the material shown in FIG. 5 of the drawings. Because the stent 50 is made up of a plurality of individual segments 51 and 56, there is no particular need for additional openings in the wall of the stent, the spaces between the segments providing adequate openings for initial fluid drainage and subsequent epithelialization.

Simply by way of example, FIGS. 10 and 12 illustrate the inclusion of a filament 60 in the wall of the stent. The purpose of the filament 60 is to show that the stent 50 can be made of a plastic material having sufficient memory to be urged to the open condition as shown in FIG. 12; or, the stent 50 can be made of a relatively flaccid fabric or the like having spring filaments 60 embedded therein for urging the stent 50 to its open position. Also, the stent 50 can be made entirely of metal, including well known alloys of platinum and gold, or chromium and cobalt.

From the foregoing discussion it will be understood that the present invention provides an arterial stent and a method for placing the stent for preventing re-stenosis following angioplasty or other mechanical opening of the lumen in an artery. While several specific designs and materials have been disclosed, those skilled in the art will recognize that the materials must be implantable, and all portions of the stent must be sufficiently smooth to prevent trauma during placement. Further, all corners and the like should be well rounded to promote epithelialization without subsequent trauma due to the presence of sharp edges during natural body motions.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

I claim:

1. An implantable intralumenal stent for use in maintaining an opening along a damaged vessel, said stent comprising:

a sleeve having a spiral wall, said wall defining an inner longitudinal edge portion and an outer longitudinal edge portion for allowing said sleeve selectively to assume a first contracted spiral position wherein said inner longitudinal edge portion is spiraled inwardly of said outer longitudinal edge portion for providing a collapsed diameter of the sleeve and the sleeve is small enough to move longitudinally through a vessel, and a second expanded position where said inner longitudinal edge position is moved outwardly for providing an expanded diameter for said sleeve and the sleeve is large enough to engage and support the vessel;

means for urging said wall toward said collapsed diameter; and locking means for holding said wall in said expanded position and preventing motion of said wall toward said collapsed diameter, said locking means including a plurality of lugs positioned on an outer surface of the inner longitudinal edge portion and an inner surface of the outer longitudinal edge portion of said wall, said wall being formed with an array of openings therein for promotion of epithelialization and the incorporation of the stent into the vessel.

2. The implantable intralumenal stent of claim 1, wherein said wall defining an array of openings therein includes a plurality of wall segments, and a spine connecting said wall segments, whereby said stent is readily bendable along a longitudinal axis with the bending being resisted only by the spine.

3. The implantable intralumenal stent of claim 1, wherein said means for urging said wall toward said collapsed diameter comprises an elastic force inherent in a material used to make said wall.

4. An implantable intralumenal stent for use in maintaining an opening along a damaged vessel, said stent comprising a sleeve having a spiral wall, said wall defining an inner longitudinal edge portion and an outer longitudinal edge portion, with said edge portions defining a gap for allowing said sleeve selectively to assume a first contracted spiral configuration wherein said inner longitudinal edge portion is spiraled inwardly of said outer longitudinal edge portion for providing a collapsed diameter of the sleeve and the sleeve is small enough to move longitudinally through a vessel, and a second approximately cylindrical expanded configuration wherein said inner longitudinal edge portion is moved outwardly for providing an expanded diameter of said sleeve and the sleeve is large enough to engage and support the vessel, means for urging said wall toward said expanded diameter, and locking means for preventing motion of said wall by said means for urging said wall toward said expanded diameter, said wall being formed with an array of openings therein for promotion of epithelialization and the incorporation of the stent into the vessel.

5. The implantable intralumenal stent of claim 4, wherein said wall defining an array of openings therein includes a plurality of wall segments, and a spine connecting said wall segments, whereby said stent is readily bendable along a longitudinal axis, with the bending being resisted only by the spine.

\* \* \* \* \*